United States Patent
Tsuchikura et al.

(10) Patent No.: US 9,987,119 B2
(45) Date of Patent: Jun. 5, 2018

(54) VASCULAR PROSTHESIS

(71) Applicant: Toray Industries, Inc., Tokyo (JP)

(72) Inventors: Hiroshi Tsuchikura, Otsu (JP); Satoshi Yamada, Otsu (JP); Takayuki Kaneko, Nagoya (JP); Atsushi Kuwabara, Otsu (JP); Yuka Sakaguchi, Otsu (JP); Koji Kadowaki, Otsu (JP); Motoki Takaoka, Otsu (JP)

(73) Assignee: Toray Industries, Inc. (JP)

( * ) Notice: Subject to any disclaimer, the term of this patent is extended or adjusted under 35 U.S.C. 154(b) by 0 days. days.

(21) Appl. No.: 15/502,518

(22) PCT Filed: Jun. 17, 2015

(86) PCT No.: PCT/JP2015/067407
§ 371 (c)(1),
(2) Date: Feb. 8, 2017

(87) PCT Pub. No.: WO2016/024441
PCT Pub. Date: Feb. 18, 2016

(65) Prior Publication Data
US 2017/0224466 A1    Aug. 10, 2017

(30) Foreign Application Priority Data
Aug. 12, 2014    (JP) .................................. 2014-164367

(51) Int. Cl.
*A61F 2/06* (2013.01)
*A61L 27/18* (2006.01)

(52) U.S. Cl.
CPC ................ *A61F 2/06* (2013.01); *A61L 27/18* (2013.01)

(58) Field of Classification Search
CPC combination set(s) only.
See application file for complete search history.

(56) References Cited

U.S. PATENT DOCUMENTS

| | | |
|---|---|---|
| 3,350,488 A | 10/1967 | Breen |
| 3,531,368 A | 9/1970 | Okamoto et al. |
| 4,695,280 A | 9/1987 | Watanabe et al. |
| 5,163,951 A | 11/1992 | Pinchuk et al. |
| 5,697,969 A | 12/1997 | Schmitt et al. |
| 2005/0240261 A1 | 10/2005 | Rakos et al. |

(Continued)

FOREIGN PATENT DOCUMENTS

| | | |
|---|---|---|
| CA | 2 933 676 A1 | 6/2015 |
| EP | 0 587 461 A2 | 3/1994 |
| EP | 3 075 351 A1 | 10/2016 |

(Continued)

*Primary Examiner* — Christopher D Prone
(74) *Attorney, Agent, or Firm* — DLA Piper LLP (US)

(57) ABSTRACT

A double-weave vascular prosthesis includes an inner layer that contacts a flow of blood, and an outer layer in contact with the inner layer and having an inner layer-covering rate C (%) of 15%≤C≤75% defined by formula (1):

$$C=[\{(W1 \times D1 + W2 \times D2) \times 25.4 - W1 \times W2 \times D1 \times D2\}/(25.4 \times 25.4)] \times 100 \quad (1),$$

where D1 is a warp density (ends/25.4 mm) of the outer layer, D2 is a weft density (picks/25.4 mm) of the outer layer, W1 is an apparent width (mm) of a warp yarn of the outer layer, and W2 is an apparent width (mm) of a weft yarn of the outer layer, and the apparent width of each yarn is determined as a mean of measurement values for the widths of randomly selected five threads exposed on a surface of the woven structure.

5 Claims, 1 Drawing Sheet

(56) References Cited

U.S. PATENT DOCUMENTS

2009/0088828 A1   4/2009   Shalev et al.

FOREIGN PATENT DOCUMENTS

| JP | 61-4546 B2 | 2/1986 |
| JP | 61-58190 B2 | 12/1986 |
| JP | 63-115555 A | 5/1988 |
| JP | 5-337143 A | 12/1993 |
| JP | 6-506369 A | 7/1994 |
| JP | 07-299084 A | 11/1995 |
| JP | 2008-540022 A | 11/2008 |
| WO | 2015/080143 A1 | 6/2015 |
| WO | 2015/093480 A1 | 6/2015 |

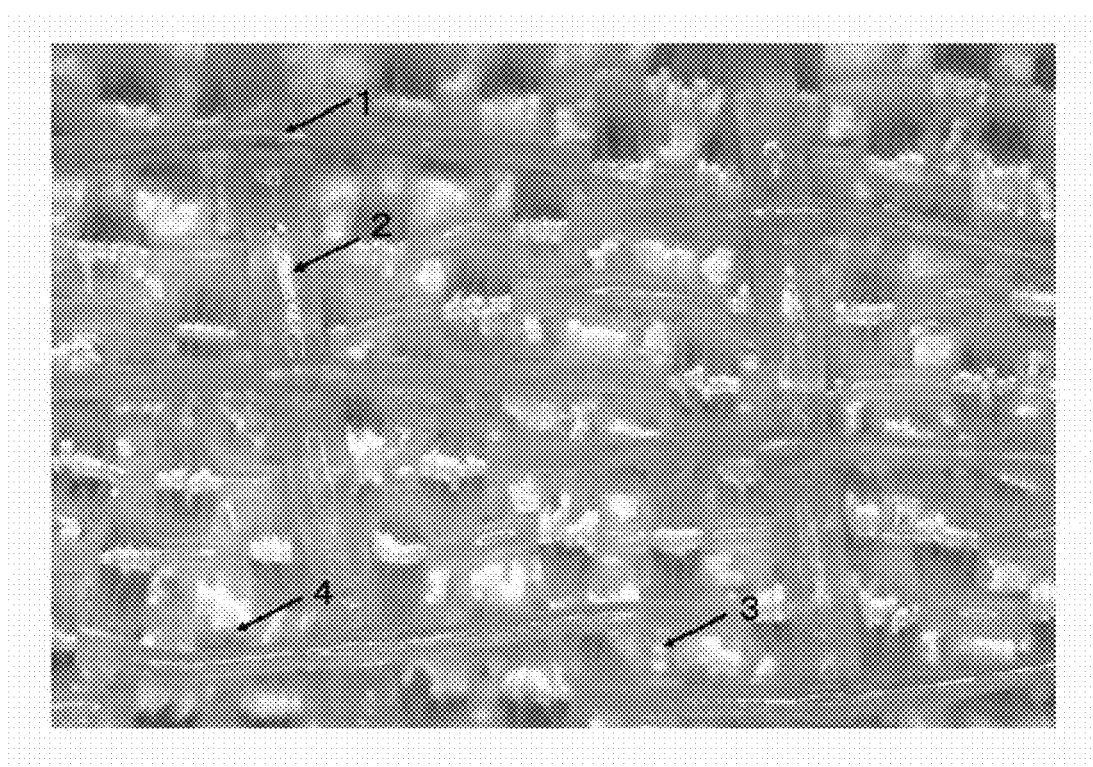

VASCULAR PROSTHESIS

TECHNICAL FIELD

This disclosure relates to a vascular prosthesis. In particular, the disclosure relates to a textile vascular prosthesis having a repair function similar to that of blood vessels in a living body and relies on spontaneous healing ability of a human body.

BACKGROUND

Vascular prostheses are used in adults mainly to replace pathological blood vessels in the body and create a bypass or a shunt, and are used in children mainly to create a shunt. Vascular prostheses are thus required to be highly biocompatible and non-toxic, durable and non-degradable in a living body, flexible, substantially non-permeable to blood, and highly effective in promoting the settlement of adherent vascular endothelial cells.

Accordingly, vascular prostheses with elasticity similar to that of blood vessels in a living body have been proposed. For example, JP H05-337143 A describes a vascular prosthesis comprising a main body and a helical reinforcement therefor that are both elastic. JP H07-299084 A describes an artificial prosthesis (vascular prosthesis) comprising an elastic porous body made of a polyester resin as a support and a composite structure arranged on at least part of the support, the composite structure being provided with a porous layer of an elastic resin. The vascular prostheses described in JP '143 and JP '084, however, have a thin film-like structure made of a resin material and thus suffer from a drawback of poor flexibility. These vascular prostheses also have a multilayer structure in the cross-sectional direction of the vessel that increases shape retainability and prevents blood leakage. Such a multilayer structure, however, creates a distance between the blood vessel's innermost layer and the peripheral tissue. Endothelium should be formed on the innermost layer, but the distance becomes an obstacle to delivery of essential substances from the peripheral tissue to the innermost layer. Consequently, the blood vessel has poor compatibility with the human body. JP '143 also describes that the main body of the vascular prosthesis and the elastic reinforcement are made of polyurethane. However, in long-term implantation, polyurethane is degraded by hydrolysis and gradually loses elasticity. Due to this drawback, the vascular prosthesis is disadvantageously required to be replaced with a new one at a certain timing.

Regarding the above requirements for vascular prostheses, vascular endothelial cells play a key role. Vascular endothelial cells constantly produce nitrogen monoxide and prosta-glandin to inhibit platelet aggregation and control the platelet function and coagulation and fibrinolytic system, thereby preventing thrombus formation in the blood vessels. Hence, high effectiveness in promoting the settlement of adherent vascular endothelial cells is a very important characteristic of vascular prostheses.

Conventional textile vascular prostheses are typically made of a woven or knitted fabric of chemical fibers such as polyester. Many are made of a very high density woven or knitted fabric, i.e., a tightly woven or knitted fabric to prevent leakage of blood through their walls and maintain their shapes. However, conventional textile vascular prostheses suffer from slow and uneven formation of a vascular endothelial cell layer. That is, in conventional textile vascular prostheses, thick fibers are tightly woven or knitted, which provides only a few scaffolds for formation of a vascular endothelial cell layer. In addition, even though some cells adhere to the inner wall, most of them tend to be easily washed away by the blood flow, which may result in formation of an occluding thrombus in a narrow blood vessel in the periphery.

Various proposals have been made to enhance settlement of adherent vascular endothelial cells in vascular prostheses. One of the proposals is, for example, a vascular prosthesis having raised microfibers of 0.5 denier or less on the inner wall as described in JP S61-4546 B. Another proposal is a vascular prosthesis having raised microfibers of 0.5 denier or less on the inner wall and/or the outer wall and comprising a ground structure made of a ground yarn containing fibers of 1.0 denier or more as described in JP S61-58190 B.

However, formation of raised microfibers on the inner wall as described in JP '546 and JP '190, does not sufficiently enhance settlement of adherent cells. The raised fibers may inversely inhibit growth of the adherent cells.

It could therefore be helpful to provide a textile vascular prosthesis having various properties required of it and having a repair function similar to that of blood vessels in a living body and relies on spontaneous healing ability of a human body.

SUMMARY

We thus provide:

(1) A double-weave vascular prosthesis with tubular woven structure, the prosthesis comprising an inner layer to be in contact with a blood flow, and an outer layer being in contact with the inner layer and having an inner layer-covering rate C (%) of $15\% \leq C \leq 75\%$.

The inner layer-covering rate C (%) is defined by the formula:

$$C=[\{(W1 \times D1+W2 \times D2) \times 25.4-W1 \times W2 \times D1 \times D2\}/(25.4 \times 25.4)] \times 100,$$

where D1 is the warp density (ends/25.4 mm) of the outer layer, D2 is the weft density (picks/25.4 mm) of the outer layer, W1 is the apparent width (mm) of a warp yarn of the outer layer, and W2 is the apparent width (mm) of a weft yarn of the outer layer.

The apparent width of each yarn is determined as a mean of measurement values for the widths of randomly selected five threads exposed on the surface of the woven.

(2) The vascular prosthesis according to the above (1), wherein the inner layer comprises warp and weft yarns that are microfiber multifilament yarns with a monofilament diameter of from 1 μm to 8 μm.

(3) The vascular prosthesis according to the above (1) or (2), wherein the warp and weft yarns of the outer layer have a monofilament fineness of 20 dtex or more.

(4) The vascular prosthesis according to the above (3), wherein the warp and weft yarns of the outer layer are each a monofilament yarn.

(5) The vascular prosthesis according to the above (4), wherein the monofilament yarn in the outer layer is made of a polyester fiber.

A conventionally known vascular prosthesis utilizes microfiber multifilament yarns in an inner layer to be in contact with the blood flow to increase compatibility with vascular endothelial cells. A known multiple ply woven vascular prosthesis is formed by arranging fibers with high flexural rigidity in an outer layer to provide structural strength. However, when a vascular wall has a multilayer structure composed of dense inner and outer layers, the peripheral tissue surrounding the vascular prosthesis adheres only to the outer layer and is separated from vascular endothelial cells. Hence, various functions that should be provided from the capillary vessels and the like to the vascular prosthesis cannot be efficiently imparted.

In such a multilayer structure, adhesion of the peripheral tissue to the outer layer and formation of endothelial cells on the inner layer may be accompanied by the creation of empty space intermittently extending between the outer layer and the inner layer. Due to the empty space, when the vascular prosthesis is physically bent, a wrinkle may be formed on the inner layer and may inhibit the blood flow; or when a hole is generated on the vascular prosthesis by an injection or the like, the blood may flow into the empty space.

In contrast, our vascular prosthesis has an outer layer provided with desired structural strength and pores that allow an inner layer to be in direct contact with the peripheral tissue. Thus, the vascular prosthesis can be fused to a human body shortly after implantation. The human body tissue can closely adhere to the inner and outer surfaces of the single thin woven structure and, therefore, even when the wall surface of the vascular prosthesis is damaged by an injection or the like after implantation, the vascular prosthesis exhibits a repair function similar to that of blood vessels in a living body, relying on spontaneous healing ability of the human body.

BRIEF DESCRIPTION OF THE DRAWING

FIG. 1 shows a photograph of a vascular prosthesis at a 150-fold magnification.

REFERENCE SIGNS LIST

1 Warp yarn forming the outer layer
2 Weft yarn forming the outer layer
3 Warp yarn forming the inner layer
4 Weft yarn forming the inner layer

DETAILED DESCRIPTION

Examples of our prostheses will be described below.
Outer Layer Having an Inner Layer-Covering Rate C (%) of 15%≤C≤75%

An important feature of the vascular prosthesis is a thin woven structure. FIG. 1 shows a photograph of a vascular prosthesis at a 150-fold magnification, taken from the outer layer side. The numeral 1 indicates a warp yarn forming the outer layer, the numeral 2 indicates a weft yarn forming the outer layer, the numeral 3 indicates a warp yarn forming the inner layer, and the numeral 4 indicates a weft yarn forming the inner layer. As shown in FIG. 1, the outer layer has a mesh-like structure.

The inner layer is positioned on the inside of the vascular prosthesis and is to be in contact with a flow of blood. The inner layer serves as a scaffold for the adhesion of vascular endothelial cells. The inner layer with a more dense structure with a smaller gap between the warp and weft fibers provides a larger number of scaffolds for the adhesion of vascular endothelial cells. A large gap between the warp and weft fibers is disadvantageous because leakage of blood from the implanted vascular prosthesis may occur, may not be stopped, and may pose a risk of a large amount of bleeding. In contrast to the inner layer, the outer layer is only required to have a structure with appropriate shape retainability as well as appropriate strength and durability. If the outer layer has an excessively dense structure, the peripheral tissue surrounding the vascular prosthesis adheres only to the outer layer and does not reach the inner layer. Consequently, the peripheral tissue is separated from vascular endothelial cells, and various functions that should be provided from the capillary vessels and the like to the vascular prosthesis cannot be efficiently imparted.

Accordingly, the outer layer serving as the skeleton does not have a dense structure, but is required to have a small inner-layer covering rate so that the vascular prosthesis can be fused to a human body shortly after implantation. The term "inner layer-covering rate" refers to the percentage of the coverage of the inner layer by the outer layer. The inner layer-covering rate is defined by the warp and weft densities of the outer layer and the apparent widths of the yarns of the outer layer, as described above. The inner layer-covering rate is preferably 75% or less, and more preferably 15% or more. The vascular prosthesis with an inner layer-covering rate of 75% or less has a large number of pores on the outer layer. This structure facilitates direct contact of the peripheral tissue with the inner layer, and allows the vascular prosthesis to be fused to the human body shortly after implantation. While the surface structure of the inner layer is sufficiently dense to prevent leakage of blood, the vascular prosthesis's function as a textile allows the capillary vessels of the peripheral tissue to grow into the vascular prosthesis. The vascular prosthesis, thus, exhibits material exchange capacity similar to that of blood vessels in a living body. As a result, the peripheral tissue closely adheres to the woven inner layer, which promotes the integration of the vascular prosthesis into a living body. In addition, since human body tissue closely adheres to the inside and outside of the woven inner layer, the vascular prosthesis exhibits a repair function similar to that of blood vessels in a living body relying on spontaneous healing ability of the human body, and no empty space exists between the peripheral tissue and the inner layer of the vascular prosthesis. Hence, even when the wall surface of the vascular prosthesis is damaged by injection or the like after implantation, the vascular prosthesis can stop the leakage and bleeding of blood therefrom simultaneously with repairing the peripheral tissue. Further, only the woven inner layer is present between the peripheral tissue and endothelial cells and, thus, even when the peripheral tissue is moved along with the movement of muscles and the like, the inner layer of the vascular prosthesis can follow the movement. This function greatly reduces the risk of occurrence of a wrinkle on the inner layer, which is softer than the outer layer. From the above reasons, the inner layer preferably has a thin woven structure with a sufficient density to prevent leakage of blood.

However, a too low covering rate of the inner layer by the outer layer is disadvantageous because the volume of the fibers in the outer layer may not be sufficient to support the outer layer structure itself, and in turn the vascular prosthesis may cause compression and strength deterioration. Accordingly, the inner layer-covering rate is preferably 15% or more.

The inner layer-covering rate depends on the intended duration of the usage of the vascular prosthesis and the health conditions of a human who is to be subjected to implantation. However, in view of the strength of adhesion to the peripheral tissue, maintenance of the structural strength and shape retainability, the inner layer-covering rate is more preferably from 20% to 60%.

Warp and Weft Yarns of Inner Layer are Microfiber Multifilament Yarns with a Monofilament Diameter of From 1 μm to 8 μm The warp and weft yarns of the inner layer are preferably microfiber multifilament yarns with a monofilament diameter of 8 μm or less. With use of such microfiber multifilament yarns as the warp and weft yarns of the inner layer, the flexural rigidity of the fibers is reduced, the weave density can be increased, and the monofilaments are easily closely packed. In this manner, the voids between the fibers in the inner layer are reduced and, in turn, leakage of blood is more efficiently prevented. In addition, the inner layer provides a large number of scaffolds suitable for adhesion of vascular endothelial cells. As a result, vascular endothelial cells are well settled on the structural fibers of the inner layer of the vascular prosthesis, and vascular endothelial cells well adhere to the inner layer of the vascular prosthesis. Inversely, when the monofilament diameter is less than 1 μm, adhesion of endothelial cells tends to be inhibited. Accordingly, the warp and weft yarns of the inner layer preferably are microfiber multifilament yarns with a monofilament diameter of 1 μm or more.

Warp and Weft Yarns of Outer Layer are Monofilament Yarns with a Monofilament Fineness of 20 dtex or More Depending on the type of the polymer used as the material of the yarns, deterioration of the strength due to hydrolysis is of concern and, therefore, the monofilament fineness of the warp and weft yarns of the outer layer is preferably 20 dtex or more. Too thick yarns, when used in the outer layer, reduce the warp and weft densities and locally cause uneven stiffness and, therefore, typically the monofilament fineness is preferably 300 dtex or less. To enhance kink resistance and shape retainability, more preferably the warp yarn is 100 dtex or less and the weft yarn is 100 dtex or more. The warp and weft yarns used to form the outer layer may be multifilament yarns, but monofilament yarns are preferred because a stable woven structure can be obtained, and the apparent widths of the yarns can be minimized, which enhances accessibility of the peripheral tissue to the inner layer. Use of a monofilament yarn enhances maintenance of the shape and strength of the vascular prosthesis and prevents bending (increases kink resistance). Exposure of the monofilament yarn on the surface of the inner layer is not preferred because the exposed monofilament yarn may inhibit the growth of endothelial cells and may become a starting point of leakage of blood and thrombus formation. The important feature is that the vascular prosthesis is provided as a double weave structure where the woven inner layer structure is always present between the monofilament yarns and the flow of blood.

The microfiber multifilament yarn used to form the inner layer may be a single type or a combination of different types of microfiber multifilament yarns with different monofilament finenesses and different total finenesses.

As the microfiber multifilament yarn, so-called direct spun yarn may be directly used, or a splittable yarn may be used. The splittable yarn may be one that can be made into ultra-fine fibers by chemical or physical means. The ultra-fining process may be performed after the tubular woven fabric is formed. The ultra-fining process by chemical or physical means may be done by, for example, removing one of the components in composite fibers or by splitting composite fibers into their respective segments, thereby giving fibrils or ultra-fine fibers, as described in U.S. Pat. Nos. 3,531,368 and 3,350,488. By the process, fibers with a common thickness at the time of the formation of the multiple ply tubular woven fabric can be made into ultra-fine fibers at a later process. Consequently, troubles that may occur during various processing, for example, breakage of a yarn and formation of lint during the weaving process or during various yarn processing before weaving, are minimized.

The vascular prosthesis is a vascular prosthesis with a tubular woven structure comprising the inner layer to be in contact with a flow of blood, and the outer layer being in contact with the inner layer. The double-weave vascular prosthesis with the tubular woven structure is preferably formed by weaving two layers together by a usual technique such as binding of the inner layer with the warp, binding of the inner layer with the weft, and binding with the multiple wefts.

Various types of organic fibers may be used as the fibers to form the inner and outer layers of the vascular prosthesis. When elasticity is desired, polyurethane fibers or the like can be used, but in terms of water absorptivity and degradation resistance, polyester fibers are preferred. Examples of the polyester fibers include polyethylene terephthalate fibers, polybutylene terephthalate fibers and the like. The polyester fibers may be copolymerized polyester fibers produced by copolymerizing polyethylene terephthalate or polybutylene terephthalate with an acid component, for example, isophthalic acid, sodium 5-sulfoisophthalate, or an aliphatic dicarboxylic acid such as adipic acid.

The loom to be used may be a water-jet loom, an air-jet loom, a rapier loom, a shuttle loom or the like. Of these, preferred is a shuttle loom, which is excellent in weaving a tubular fabric and can give a uniform tubular structure. The weave pattern of the double-weave vascular prosthesis may be plain weave, twill weave or sateen weave, or modified weave thereof, or multiple ply weave. The basic weaving process may be a known process.

The vascular prosthesis can be used for applications involving loading an antithrombotic agent on the vascular prosthesis. The antithrombotic agent loaded on the vascular prosthesis may be, for example, an organism-derived anticoagulant such as heparin, low-molecular-weight heparin, urokinase, and hirudin; a synthetic anticoagulant and a synthetic antiplatelet such as argatroban, warfarin, acetylsalicylic acid ticlopidine and the like. The vascular prosthesis may be loaded with a hydrophilic polymer such as polyethylene glycol, polyvinyl alcohol, and polyvinylpyrrolidone. The loading may be performed by any method, and may be done by, for example, coating the surface of the multifilament yarn with a solution containing the above drug or polymer; or fixing the drug or polymer on the surface of the multifilament yarn through chemical reaction such as condensation reaction, using a reactive functional group chemically introduced into the drug or polymer; or fixing the drug or polymer by radical reaction using a high energy beam; or filling the voids in the multifilament yarn with the drug or polymer through impregnation of the yarn with collagen, gelatin or hydrogel containing the drug or the polymer; or other methods. Loading an ionic compound such as heparin may be done by, for example, coating the surface of the multifilament yarn with a salt of the ionic compound formed with a counterion, or binding the counterion of the ionic compound to the surface of the multifilament yarn and then binding the ionic compound to the counterion by ionic interaction. In terms of imparting high antithrombotic activity and stably maintaining the antithrombotic activity for a long period of time, preferred are a method in which the drug or polymer is fixed on the surface through chemical reaction using a reactive functional group chemically introduced into the drug or polymer, and a method in which the counterion of the drug or polymer is bound to the surface followed by ionic binding of the drug or polymer to the counterion. Loading the drug or polymer on the multifilament yarn, as described above, to impart antithrombotic activity may be performed before formation of the tubular woven fabric. However, antithrombotic activity is preferably imparted after formation of the composite tubular woven fabric in view of reduction in the production cost.

Blood pressure is maintained at a certain high level in a living body and, due to this, leakage of blood through the voids between the fibers is difficult to be avoided. Accordingly, before use of a textile vascular prosthesis in vascular surgery, so-called preclotting is often performed. Preclotting is a pre-implantation procedure in which a vascular prosthesis is brought into contact with blood for artificial formation of thrombi and temporal clogging of the voids between the fibers with the thrombi. Our vascular prosthesis can be used for applications involving preclotting.

EXAMPLES

Our prostheses will be specifically described with reference to Examples. However, this disclosure is not limited to the Examples. Various alterations and modifications are possible within the technical scope of the disclosure. The various types of the properties evaluated in the Examples were measured as follows.
(1) Monofilament Diameter of Microfiber Multifilament Yarn The total fineness of a yarn was determined as a mass-corrected fineness in accordance with method A in JIS L 1013 (2010) 8.3.1, by setting the predetermined load at 0.045 cN/dtex. The determined total fineness was divided by the number of monofilaments to give a monofilament fineness d [dtex]. From the monofilament fineness d and the specific gravity ρ of the polymer used to form the yarn, the monofilament diameter (mm) of the microfiber multifilament yarn was calculated by formula (1):

$$\sqrt{\frac{4 \times d}{10^4 \times \rho \times \pi}}. \tag{1}$$

(2) Monofilament Fineness

Total fineness of a yarn was determined as a mass-corrected fineness in accordance with method A in JIS L 1013 (2010) 8.3.1, by setting the predetermined load at 0.045 cN/dtex. The determined total fineness was divided by the number of monofilaments to give a monofilament fineness.
(3) Apparent Widths of Yarns The surface of the outer layer of a woven fabric is observed under a microscope at a 150-fold magnification, and the widths of threads around the center of the starting and finishing points of the weaving are measured. The widths of threads in the warp and weft directions were measured at randomly selected five points for each direction, and the means of the measurement values were determined as apparent widths of the yarns.

Example 1

A polyester microfiber multifilament yarn with a monofilament diameter of 4.6 μm and a total fineness of 33 dtex was prepared, and used as warp and weft yarns to form the inner layer of a tubular woven fabric in the weaving process described later.

A polyester monofilament yarn with a monofilament fineness of 44 dtex was prepared as a warp yarn, then a polyester monofilament yarn with a monofilament fineness of 180 dtex was prepared as a weft yarn, and the warp and weft yarns were used to form the outer layer of the tubular woven fabric.

A tubular woven fabric with modified twill pattern in double weave in which two layers were each composed of one set of the warp and weft were woven with a shuttle loom using the above yarns. The obtained tubular fabric with 5 mm in internal diameter was scoured at 98° C. The fabric was dry-heated at 120° C. Into the fabric, a rod mandrel was inserted and the fabric heat-set at 170° C. into that shape. The fabric was sterilized. Table 1 shows the types of yarns for forming the outer layer, the weave densities of the outer layer, the apparent widths of the yarns of the outer layer, the inner layer-covering rate, the type of yarn for forming the inner layer, and the monofilament diameter of the microfiber multifilament yarn in the inner layer of the vascular prosthesis. The thus produced vascular prosthesis with tubular woven structure was implanted into a dog. One week later, the implantation site was harvested and examined. No thrombus adhered to the vascular prosthesis. A pathological analysis showed that the growth of endothelial cells. Strong adhesion of the peripheral tissue to the vascular prosthesis was observed.

Example 2

A tubular woven fabric was produced in the same manner as in Example 1, except that the polyester warp and weft yarns used to form the inner layer were each a multifilament yarn with a monofilament diameter of 9.2 μm and a total fineness of 33 dtex, and the polyester warp yarn used to form the outer layer was a multifilament yarn with a monofilament fineness of 2.75 dtex and a total fineness of 33 dtex. Table 1 shows the types of yarns to form the outer layer, the weave densities of the outer layer, the apparent widths of the yarns of the outer layer, the inner layer-covering rate, the type of yarn to form the inner layer, and the monofilament diameter of the microfiber multifilament yarn in the inner layer of the vascular prosthesis.

The thus produced vascular prosthesis with tubular woven structure was implanted into a dog. One week later, the implantation site was harvested and examined. A few thrombi adhered to the vascular prosthesis. A pathological analysis showed that the growth of some endothelial cells. Adhesion of the peripheral tissue to the vascular prosthesis was observed. The performance of the vascular prosthesis of Example 2 was slightly inferior to that of Example 1, but the vascular prosthesis of Example 2 was a good product that was sufficiently adequate for practical use.

Example 3

A tubular woven fabric was produced in the same manner as in Example 1, except that the polyester warp and weft yarns used to form the inner layer were each a multifilament yarn with a monofilament diameter of 5.4 μm and a total fineness of 44 dtex. Table 1 shows the types of yarns to form the outer layer, the weave densities of the outer layer, the apparent widths of the yarns of the outer layer, the inner layer-covering rate, the type of yarn to form the inner layer, and the monofilament diameter of the microfiber multifilament yarn in the inner layer of the vascular prosthesis.

The thus produced vascular prosthesis with tubular woven structure was implanted into a dog. One week later, the implantation site was harvested and examined. No thrombus adhered to the vascular prosthesis. A pathological analysis showed that the growth of endothelial cells. Strong adhesion of the peripheral tissue to the vascular prosthesis was observed. The vascular prosthesis of Example 3 has a similar performance to that of Example 1 and was a good product.

Example 4

A tubular woven fabric was produced in the same manner as in Example 1, except that the polyester warp and weft yarns used to form the inner layer were each a multifilament yarn with a monofilament diameter of 2.7 μm and a total fineness of 52.8 dtex. Table 1 shows the types of yarns to form the outer layer, the weave densities of the outer layer, the apparent widths of the yarns of the outer layer, the inner layer-covering rate, the type of yarn to form the inner layer, and the monofilament diameter of the microfiber multifilament yarn in the inner layer of the vascular prosthesis.

The thus produced vascular prosthesis with tubular woven structure was implanted into a dog. One week later, the implantation site was harvested and examined. No thrombus adhered to the vascular prosthesis. A pathological analysis showed that the growth of endothelial cells. Strong adhesion of the peripheral tissue to the vascular prosthesis was observed. The vascular prosthesis of Example 4 has a similar performance to those of Examples 1 and 3 and was a good product.

Comparative Example 1

A tubular woven fabric was produced in the same manner as in Example 1, except that the polyester warp yarn used to form the outer layer was a multifilament yarn with a monofilament fineness of 1.6 dtex and a total fineness of 56 dtex. Table 1 shows the types of yarns to form the outer layer, the weave densities of the outer layer, the apparent widths of the yarns of the outer layer, the inner layer-covering rate, the type of yarn to form the inner layer, and the monofilament diameter of the microfiber multifilament yarn in the inner layer of the vascular prosthesis.

As shown in Table 1, the inner layer-covering rate of the vascular prosthesis of Comparative Example 1 was as large as 93.5%, which was largely deviated from our range. The vascular prosthesis with tubular woven structure was implanted into a dog, and one week later, occlusion of the implantation site was observed. Ultrasonic images at one day after implantation revealed that turbulent blood flow occurred due to wrinkles in the inner layer of the vascular prosthesis. This was a critical problem as a vascular prosthesis. The implantation site was harvested and examined. The peripheral tissue adhered to the outer layer, but did not reach the inner layer. Between the inner layer and the outer layer, empty space in which no human body tissue was present was observed in many areas.

Comparative Example 2

A tubular woven fabric was produced in the same manner as in Example 2, except that the polyester warp yarn used to form the outer layer was a monofilament yarn with a monofilament fineness of 10 dtex, that the polyester weft yarn used to form the outer layer was a monofilament yarn with a monofilament fineness of 44 dtex, and that the warp density of the outer layer was reduced to about ⅔.

As shown in Table 1, the inner layer-covering rate of the vascular prosthesis of Comparative Example 2 was as small as 14.1%, which was largely deviated from our range. The vascular prosthesis with tubular woven structure was implanted into a dog, and one week later, occlusion of the implantation site was observed. The tubular structure was compressed by the pressure from the peripheral tissue, and the blood flow stopped. Table 1 shows the types of yarns to form the outer layer, the weave densities of the outer layer, the apparent widths of the yarns of the outer layer, the inner layer-covering rate, the type of yarn to form the inner layer, and the monofilament diameter of the microfiber multifilament yarn in the inner layer of the vascular prosthesis.

TABLE 1

| | Types of yarns for forming outer layer | | Weave density of outer layer (ends or picks/inch) | | Apparent widths of yarns of outer layer (mm) | | Inner layer-covering rate (%) | Type of yarn for forming inner layer (warp, weft) | Monofilament diameter of microfiber multifilament yarn in inner layer (μm) |
|---|---|---|---|---|---|---|---|---|---|
| | Warp | Weft | Warp | Weft | Warp | Weft | | | |
| Example 1 | 44 dtex, 1 fil polyester | 180 dtex, 1 fil polyester | 131 | 17 | 0.064 | 0.129 | 38.8 | 33 dtex, 144 fil polyester | 4.6 |
| Example 2 | 33 dtex, 12 fil polyester | 180 dtex, 1 fil polyester | 131 | 17 | 0.12 | 0.129 | 65.2 | 33 dtex, 36 fil polyester | 9.2 |
| Example 3 | 44 dtex, 1 fil polyester | 180 dtex, 1 fil polyester | 131 | 20.5 | 0.064 | 0.129 | 40.0 | 44 dtex, 144 fil polyester | 5.4 |
| Example 4 | 44 dtex, 1 fil polyester | 180 dtex, 1 fil polyester | 131 | 17 | 0.064 | 0.129 | 38.8 | 52.8 dtex, 700 fil polyester | 2.7 |
| Comparative Example 1 | 56 dtex, 36 fil polyester | 180 dtex, 1 fil polyester | 131 | 17 | 0.18 | 0.129 | 93.5 | 33 dtex, 144 fil polyester | 4.6 |
| Comparative Example 2 | 10 dtex, 1 fil polyester | 44 dtex, 1 fil polyester | 87 | 17 | 0.03 | 0.064 | 14.1 | 33 dtex, 36 fil polyester | 9.2 |

INDUSTRIAL APPLICABILITY

Our prostheses are suitable as a vascular prosthesis used in various surgical operations.

The invention claimed is:

1. A double-weave vascular prosthesis having a substantially tubular woven structure, the prosthesis comprising an inner layer to be in contact with a flow of blood, and an outer layer in contact with the inner layer and having an inner layer-covering rate C (%) of 15%≤C≤75% defined by formula (1):

$$C=[\{(W1 \times D1+W2 \times D2) \times 25.4-W1 \times W2 \times D1 \times D2\}/(25.4 \times 25.4)] \times 100 \quad (1),$$

where D1 is a warp density (ends/25.4 mm) of the outer layer, D2 is a weft density (picks/25.4 mm) of the outer layer, W1 is an apparent width (mm) of a warp yarn of the outer layer, and W2 is an apparent width (mm) of a weft yarn of the outer layer, and the apparent width of each yarn is determined as a mean of measurement values for the widths of randomly selected five threads exposed on a surface of the woven structure.

2. The vascular prosthesis according to claim 1, wherein the inner layer comprises warp and weft yarns that are microfiber multifilament yarns with a monofilament diameter of from 1 μm to 8 μm.

3. The vascular prosthesis according to claim 1, wherein the warp and weft yarns of the outer layer have a monofilament fineness of 20 dtex or more.

4. The vascular prosthesis according to claim 3, wherein the warp and weft yarns of the outer layer are each a monofilament yarn.

5. The vascular prosthesis according to claim 4, wherein the monofilament yarn in the outer layer is made of a polyester fiber.

* * * * *